United States Patent [19]

Beisler et al.

[11] 4,058,602
[45] Nov. 15, 1977

[54] SYNTHESIS, STRUCTURE, AND ANTITUMOR ACTIVITY OF 5,6-DIHYDRO-5-AZACYTIDINE

[75] Inventors: John A. Beisler; Mohamed M. Abbasi, both of Bethesda; John S. Driscoll, Rockville, all of Md.

[73] Assignee: The United States of America as represented by the Department of Health, Education and Welfare, Washington, D.C.

[21] Appl. No.: 712,854

[22] Filed: Aug. 9, 1976

[51] Int. Cl.$^2$ ............... A61K 31/34; A61K 31/53; C07H 19/12
[52] U.S. Cl. ........................... 424/180; 536/23
[58] Field of Search ..................... 536/23; 424/180

[56] References Cited

U.S. PATENT DOCUMENTS

| | | | |
|---|---|---|---|
| 3,171,833 | 3/1965 | Sorm et al. | 536/23 |
| 3,221,010 | 11/1965 | Duschinsky | 536/23 |
| 3,462,416 | 8/1969 | Hanze et al. | 536/23 |

*Primary Examiner*—Johnnie R. Brown
*Attorney, Agent, or Firm*—John S. Roberts, Jr.; Norman J. Latker; Thomas G. Ferris

[57] ABSTRACT

The compound 5,6-dihydro-5-azacytidine, 5AC[H], and non-toxic acid addition salts such as the hydrochloride, together with its preparation from 5-azacytidine (5-AC) by reduction of the 5,6-double bond of 5-AC with an alkali metal borohydride such as sodium borohydride. Additionally, 5,6-dihydro-5-azacytidine, 5AC[H], has antitumor activity for murine leukemia systems L1210 and P388 as an injectable. In comparison with the parent compound, 5-AC, the antitumor activity is comparable and 5AC[H] exhibits a more favorable therapeutic index. It also has better solution stability over a broad pH range. A structure for the HCl salt is given below.

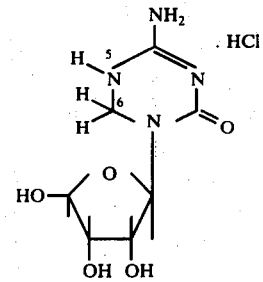

6 Claims, No Drawings

SYNTHESIS, STRUCTURE, AND ANTITUMOR ACTIVITY OF 5,6-DIHYDRO-5-AZACYTIDINE

The compounds of the present invention which are utilized therapeutically as the free base or acid addition salts are closely related to 5-azacytidine (5-AC), which is a known clinically effective anti-tumor agent limited in usefulness by its rapid hydrolysis to give products of unknown biological effect. Reduction of the 5,6-double bond of the triazine ring of 5-AC with an alkali metal borohydride such as sodium, potassium or lithium borohydride has produced 5,6-dihydro-5-azacytidine hydrochloride, 5AC[H].HC, which has excellent solution stability over a broad pH range.

Dependent upon the acid selected, a salt is produced which is a non-toxic mineral acid or organic acid which conventionally can be selected from such organic acids as maleate, tartrate, citrate, acetate, benzoate, and borate. A preferred procedure is to produce a mineral acid addition salt as with hydrochloric acid to produce the hydrochloride and, if desired, convert by substitution to produce the maleate, etc.

PRIOR ART
LITERATURE

1. John A. Beisler et al, "The Synthesis, Structure, and Antitumor Activity of 5,6-Dihydro-5-Azacytidine Hydrochloride," ACS Abstract, In Press, August 1976.
2. J. Skoda, "Azapyrimidine Nucleosides," *Antineoplastic and Immunosuppressive Agents*, Part II (Sartorelli and Johns, eds), Berlin, Springer-Verlag, 1975, pp 348–372.
3. F. Sorm et al, Experientia, 20, 202 (1964).
4. A. Piskala and F. Sorm, *Coll. Czech. Chem. Commun.*, 29, 2060 (1964).

Patents

U.S. Pat. No. 3,171,833 Sorm et al
Czech Pat. No. 114,716 Sorm et al (CA 64, 11303 (1966)
Czech Pat. No. 116,297 Sorm et al (CA 65, 795 (1966)
German Pat. No. 1,935,027 Piskala et al (CA 73, 35710 (1970)
French Pat. No. 2,123,632 (CA 78, 136627 (1973)

The compounds described above in the literature and patent art, largely of Czech origin, describe the basic compound, 5-azacytidine (NSC 102816), but lack a teaching of the 5,6-dihydro-5-azacytidine and its acid addition salts, which subject matter is covered by this invention.

The compounds of the present invention have excellent stability over a broad pH range and exhibit satisfactory antileukemic activity in animal test systems comparable to the parent compound 5-azacytidine.

THE PREPARATION

The reduction of 5-azacytidine (5-AC) was accomplished with an alkali metal borohydride such as sodium borohydride in hexamethylphosphoramide solution to produce the reduced nucleoside as a boron complex. The combination of the particular reducing agent with the solvent gave superior results in the preparation. Hydrolysis of the complex with hydrochloric acid yielded the desired 5,6-dihydro-5-azacytidine as the hydrochloride salt (5-AC[H].HCl, mp 180°–181° (decomp.), $\lambda_{max}$ (pH 8) 233 nm (log$\epsilon$ 4.98). The structure assigned to 5-AC[H] is fully supported by data from NMR, GC-MS, and combustion analysis data as well as by chemical degradation studies.

The free base of 5-AC[H] with a mp of 218°–220° may be prepared from ammonia treatment of 5-AC[H].HCl and produced a compound of good yield (89%) and purity. With reference to the acid salts, utilization of another acid similarly results in a different acid addition salt such as with a mineral acid or a non-toxic organic acid selected from maleate, tartrate, citrate, acetate, benzoate, borate, etc.

5-AC[H].HCl was also prepared from the reaction of bis[trimethylsilyl]-5-azacytosine and substituted ribofuranose derivatives followed by alkali metal borohydride reduction and hydrolysis of the product.

PHARMACOLOGICAL CHARACTERISTICS

The present compounds as well as the parent 5-azacytidine are pyrimidine nucleoside antimetabolites which find usefulness as anti-neoplastic drugs. It is noted that the 5-AC itself is of limited value in solid tumors but has been found effective in the treatment of acute leukemia. The difficulty with 5-AC has been that it decomposes quite readily in water or aqueous formulation, giving products of unknown toxicity and making strict control of dosages difficult as with a continuous infusion technique.

VARIATION AND UTILITY IN VIVO

The rapid decomposition mechanism of 5-AC in aqueous solution prompted the present researchers to produce a reduced compound where the reduction occurred at the 5,6-double bond as a means to increase the stability of the drug toward hydrolysis. It was and is theorized that in the body the reduced nucleoside of the present invention could be converted to 5-AC as a consequence of in vivo oxidation. The preparation of the reduced nucleoside is described above.

METHOD OF ADMINISTRATION AND DOSAGE

The method of administration in mice is by injection. The active doses in mice by injection against the L1210 murine tumor system on the QD 1–9 daily treatment schedule are 6.25–400 mg/kg, with an optimal dose at 100 mg/kg.

The optimum dose against L1210 on the Q4D (days 1, 5, 9) treatment schedule was 600 mg/kg, which approximates a 200 mg/kg daily dose for 9 days.

The optimum dose against the murine P388 tumor system was 200 mg/kg on the QD 1–9 daily treatment schedule.

A potential method of administration of 5AC[H] and its salts is by the oral route because of the good stability of the drug in acidic solutions. This compound and acid addition salts are active orally in a dose range of 200–1000 against L1210 in mice on a QD 1–9 schedule.

EXAMPLE 1

Synthesis of (5-AC[H]) (5,6-dihydro-5-azacytidine) (4-amino 5,6-dihydro-1-β-D-ribofuranosyl-1,3,5-triazin-2(1H)-one hydrochloride)

In the nomenclature describing the hydrochloride salt, other common non-toxic acid addition salts are also included and the free base is denoted by 5AC[H].

A solution of 4.88 gm (0.02 mole) of 5-AC in 20 ml of hexamethylphosphoramide (HMPA) was treated with 1.52 gm (0.04 mole) of sodium borohydride and stirred at 50° C for 1 hour and then at room temperature for 3 hours. The reaction was hydrolyzed with 50 ml each of methanol and water and allowed to stand at 0° overnight. Concentration of the solution under vacuum (bath temperature 30° C) gave a syrup which was washed with ether and the residue taken up in 70 ml of methanol. The boron complex which was produced as a white powder (3.81 gm) was precipitated by careful addition of ether (70 ml). Evaporation of the supernatent liquid and subjecting the residue to another ether methanol precipitation provided an additional 0.33 gm of the boron complex. Total yield 79%, melting point >330° (darkened 260°).

A solution of the boron complex (4.60 gm, 0.017 mole) in 40 ml of 6N hydrochloric acid was stirred at 21° for 4 hours. Ethanol (70 ml) was added and stirring was continued at −10° for 1 hour to give a white precipitate which was removed by filtration and washed successively with ethanol and ether. On standing, the filtrate gave a second crop. Total yield of 5AC[H].HCl was 4.05 gm (85%), melting point 180°–181° (dec.) Recrystallization from a 1:1 mixture of methanol:ethanol gave colorless needles, melting point 180°–181° (dec.) $[\alpha]_D^{29°} -27°$ [c 1.0, H$_2$O]; UV $\lambda_{max}$(pH 2) end adsorption; $\lambda_{max}$ (pH 8) 233 nm (log ϵ 4.98); NMR (dimethyl sulfoxide-d$_6$) δ 5.54 (d,J=6Hz, C$_1$, H), 4.69 (s, 2H, C$_6$H).

EXAMPLE 2

Solution Stability of the Compound as the Hydrochloric Acid Addition Salt

The solution stability of 5-AC[H].HCl at pH 2 and 6 was followed over a 3-week period using an NMR method for analysis. A 0.18M solution of 5-AC[H] containing 0.1M KCl gave a solution (pH 2.0) which was lyophilized and dissolved in D$_2$O. Lyophilization and dissolution in D$_2$O was repeated several times to completely exchange labile protons. The final lyophilizate was dissolved in the volume of 100% D$_2$O necessary to make a solution having the initial concentrations of 5-AC[H] and KCl.

In a similar way, a second sample of 5-AC[H].HCl was prepared (pH 6.0) with phosphate buffer, exchanged with deuterium, and dissolved in 100% D$_2$O affording a solution 0.17M in 5-AC[H] and 0.05M each in KH$_2$PO$_4$ and Na$_2$HPO$_4$. Integrated NMR spectra of each solution were recorded immediately and at regular intervals thereafter, using an internal standard of CHCl$_3$—CCl$_4$ (1:1) sealed in 1 mm ID glass capillary tubes. Between determinations, the NMR sample tubes were stored at 24°–25° C and at normal room illumination. Over the 3-week observation period no change in either sample was noted as demonstrated by a comparison of the integrated areas of the internal standard with the ribosyl anomeric proton, the methylene protons of the triazine ring, and the remaining non-exchangeable protons of the ribose moiety. Although 5-AC[H].HCl has a water solubility of >200 mg/ml, the free base is soluble in water to the extent of about 16 mg/ml. A solution of 5-AC[H].HCl in 1N NH$_4$OH (pH 11.8) was stored at 25° for 7 days and showed no decomposition evidence (TLC). The free base 5-AC[H] (mp 218°–220°), NSC — 265483) was isolated from the solution in good yield and purity. By contrast, a solution of 5-AC in 1N NH$_4$OH is completely decomposed in several hours.

EXAMPLE 3

Biological Evaluation

The L1210 leukemia system was used to evaluate the antitumor activity of 5-AC[H].HCl according to the protocols set out by the Division of Cancer Treatment, National Cancer Institute [Geran et al, Protocols for Screening Chemical Agents and Natural Products Against Animal Tumors and Other Biological Systems (3 ed.) Cancer Chemother Rep Part 3, vol 3(2):1–103, 1972[. Evaluation of 5-AC[H].HCl was carried out using the Q4D (Day 1, 5, 9) treatment schedule. A control group of tumored mice treated with 5-AC was routinely run in parallel with each 5-AC[H].HCl test. The results of these tests are recorded in Table 1 as increased in life span (ILS) over untreated controls.

Conclusion. It can be seen rom Table 1 that 5-AC[H].HCl has comparable antitumor activity with 5-AC in an L1210 assay. From these data therapeutic indices (TI) for each drug can be calculated. Using the method of Skipper and Schmidt (A Manual on Quantitative Drug Evaluation in Experimental Tumor Systems, Cancer Chemother Rep 17:1–25, 1962) (TI = optimal dose for maximum ILS / lowest dose giving 40% ILS) and the requisite information from the dose-response curves, TI = 6 for 5-AC (15 mg/kg / 2.5 mg/kg) and TI = 12 for 5-AC[H] (600 mg/kg / 50 mg/kg)

Additionally, the L1210 activity using the QD 1–9 schedule gave a 116% increase in life span at a dosage of 100 mg/kg per injection. On the QD 1–9 schedule an injection is given every day 1–9 and in the Q4D schedule an injection is given every 4 days.

Antitumor activity in the P388 system on the QD 1–9 schedule gave a 100% increase in life span at a dosage of 200 mg/kg per injection.

TABLE I

Comparison of 5-AC[H] and 5-AC Against L1210 Leukemia (Q4D, 0.9% Saline Vehicle)

| | 5-AC[H], NSC 264880 | | | | 5-AC, NSC 102816 | | | |
|---|---|---|---|---|---|---|---|---|
| Dose | % ILS Control Number | | | | Dose | % ILS Control Number | | |
| mg/kg | 8884 | 8887 | 8895a | 8895b | mg/kg | 8884 | 8887 | 8895 |
| 800 | | | 96 | | 40 | toxic | 22 | 09 |
| 600 | | 104 | | 83 | 20 | 81 | 138 | 74 |
| 500 | | 81 | | | 10 | 144 | 93 | 94 |
| 400 | 62 | 75 | 80 | | 5 | 58 | 64 | 68 |
| 300 | | 64 | | 82 | | | | |
| 200 | 49 | | 72 | | | | | |
| 150 | | 64 | | 74 | | | | |
| 100 | 51 | | 61 | | | | | |
| 75 | | | | 47 | | | | |
| 50 | 35 | | 52 | | | | | |
| 37.5 | | | | 41 | | | | |
| 25 | 30 | | 27 | | | | | |
| 18.7 | | | | 31 | | | | |
| 12.5 | 29 | | 23 | | | | | |
| 6.25 | 07 | | | | | | | |

EXAMPLE 4

Proof of Structure of 5-AC[H]

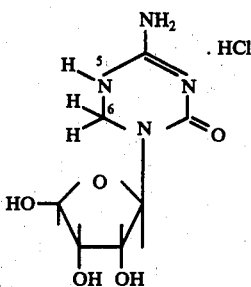

5AC[H].HCl was also prepared from the reaction of bis[trimethylsilyl]-5-azacytosine and substituted ribofuranose derivatives followed by alkali metal borohydride reduction and hydrolysis of the product.

5-AC[H].HCl was hydrolyzed with 6N HCl and produced 5,6-dihydro-5-azacytosine hydrochloride. This has a melting point of 259°–261°. In order to show the conformity of structure, 5-azacytosine hydrochloride, which is commercially available, was reduced with sodium borohydride to make 5,6- dihydro-5-azacytosine. This compound had a melting point of 189°–190°. HCl acid addition salt was formulated from the free base by treatment with HCl to produce 5,6-dihydro-5-azacytosine hydrochloride with a melting point of 259°–261° which is the same melting point as was obtained from the hydrolysis reaction. There was no depression of the mixed melting point.

NMR and gas chromatography-mass spectrometry analysis of the product from the reduction with sodium borodeuteride (used in place of sodium borohydride) confirmed the structure of the reduction product.

The reduction of $14_C$ labeled 5-azacytidine with sodium borohydride gave radiolabeled 5-AC[H].HCl.

Gas chromatography-mass spectrometry analysis also showed that 5-AC[H] could be reoxidized to produce 5-azacytidine.

We claim:

1. 5,6dihydro-5 -azacytidine and a non-toxic acid addition salt thereof wherein such salt is selected from a group consisting of non-toxic mineral acid salts and salts of organic acids selected from one member of a group consisting of maleate, tartrate, citrate, acetate, benzoate, and borate.

2. A process of reducing 5-azacytidine utilizing an alkali metal borohydride in hexamethylphosphoramide solution to produce the compound 5,6-dihydro-5-azacytidine as a boron complex and subsequently hydrolyzing said boron complex with a mineral acid to produce 5,6-dihydro-5-azacytidine as the acid salt.

3. The process of claim 2 wherein the acid is hydrochloric acid.

4. A method of inhibiting leukemia L1210 and P388 in mice which comprises utilizing an effective amount of 5,6-dihydro-5-azacytidine as an injectable in a dosage regimen of 6 mg/kg – 600 mg/kg of body weight of the compound 5,6-dihydro-5-azacytidine and a non-toxic acid addition salt thereof wherein such salt is selected from a group consisting of non-toxic mineral acid salts and salts of organic acids selected from one member of a group consisting of maleate, tartrate, citrate, acetate, benzoate, and borate.

5. The method of claim 4 wherein leukemia L1210 is inhibited.

6. The method of claim 4 wherein leukemia P388 is inhibited.

* * * * *

UNITED STATES PATENT OFFICE
CERTIFICATE OF CORRECTION

Patent No. 4,058,602　　　Dated November 15, 1977

Inventor(s) John A. Beisler, Mohamed M. Abbasi, and John S. Driscoll

It is certified that error appears in the above-identified patent and that said Letters Patent are hereby corrected as shown below:

Column 1, line 14, "5AC[H]·HC" should be --5AC[H]·HCl--

Signed and Sealed this

Twenty-eighth Day of March 1978

[SEAL]

Attest:

RUTH C. MASON
*Attesting Officer*

LUTRELLE F. PARKER
*Acting Commissioner of Patents and Trademarks*